United States Patent [19]

Gutierrez et al.

[11] Patent Number: 4,606,851

[45] Date of Patent: Aug. 19, 1986

[54] METHOD FOR IMPROVING WATER SOLUBILITY OF SURFACTANTS USING TERPENE SULFONATE HYDROTROPES

[75] Inventors: Eddie N. Gutierrez, Fort Lee; Vincent Lamberti, Upper Saddle River, both of N.J.

[73] Assignee: Lever Brothers Company, New York, N.Y.

[21] Appl. No.: 705,260

[22] Filed: Feb. 25, 1985

Related U.S. Application Data

[62] Division of Ser. No. 584,184, Feb. 27, 1984, Pat. No. 4,528,144.

[51] Int. Cl.$^4$ ............................ C11D 3/34; B01F 3/00
[52] U.S. Cl. ............................... 252/554; 252/363.5; 252/545; 252/549; 252/DIG. 14
[58] Field of Search ....... 252/549, 554, 558, DIG. 14, 252/353, 363.5, 545; 260/503

[56] References Cited

U.S. PATENT DOCUMENTS

| | | | |
|---|---|---|---|
| 2,220,678 | 11/1940 | Cromwell et al. | 260/98 |
| 2,243,331 | 5/1941 | de Simo et al. | 260/513 |
| 2,318,036 | 5/1943 | Werntz | 260/503 |
| 3,332,880 | 7/1967 | Kessler et al. | 252/161 |
| 3,929,680 | 12/1975 | Arai et al. | 252/542 |
| 4,137,257 | 1/1979 | Traynor | 260/503 |
| 4,224,240 | 9/1980 | Kane et al. | 260/503 |
| 4,283,347 | 8/1981 | Kane et al. | 260/429.9 |
| 4,524,022 | 6/1985 | Naylor | 252/548 |

OTHER PUBLICATIONS

Traynor et al., J. Org. Chem., vol. 44, p. 1557 (1979).
Starks, J. Amer. Chem. Soc., vol. 93, p. 195 (1971).

*Primary Examiner*—Prince E. Willis
*Attorney, Agent, or Firm*—Milton L. Honig; James J. Farrell

[57] ABSTRACT p-Menthane-7-sulfonic acid and p-menthane-2-sulfonic acid and their alkali metal, alkaline earth metal, ammonium and alkylolammonium salts are disclosed. A method for increasing the solubility of an only partially water-soluble material is presented comprising combining the material in water with the salts of p-menth-6-ene-2-sulfonic acid, p-menth-1-ene-7-sulfonic acid and their saturated derivatives as hydrotropes. p-Menth-6-ene-2-sulfonate salts are prepared from α-pinene and sulfite or bisulfite salt in the presence of a phase transfer catalyst under free radical conditions.

3 Claims, No Drawings

METHOD FOR IMPROVING WATER SOLUBILITY OF SURFACTANTS USING TERPENE SULFONATE HYDROTROPES

This is a divisional application of Ser. No. 584,184 filed Feb. 27, 1984, which matured into U.S. Pat. No. 4,528,144.

BACKGROUND OF THE INVENTION

1. Field of the Invention

This invention relates to novel p-menthane sulfonates and their use as hydrotropes in aqueous compositions.

2. The Prior Art

Many aqueous compositions contain organic components of poor water solubility. Hydrotropes are formulated into these liquids to increase the aqueous solubility of the hydrophobic organic components. Commonly employed hydrotropes include the salts of toluene, xylene or cumene sulfonates. While these commercial compounds perform satisfactorily, there is a need for lower cost alternatives, especially materials not derived from petrochemical feedstocks.

Among the relatively low-cost renewable raw materials is turpentine, an extract of pine trees. The $\alpha$ and $\beta$-pinenes, which are major components of turpentine, when reacted with pyrosulphuryl chloride yield sulfonate compounds as in U.S. Pat. No. 2,220,678. Traynor et al, *J. Org. Chem.*, Vol. 44, 1557, 1979, reports that sodium p-menth-6-ene-2-sulfonate (I) can be formed from the dehydration of the reaction product between sodium sulfite and the $\alpha$-pinene derivative limonene oxide. This publication further discloses that $\beta$-pinene will react with sodium bisulfite to form sodium p-menth-1-ene-7-sulfonate (II). The saturated analogs of I and II, i.e., III and IV respectively, have apparently not yet been reported. Little is known concerning the utility of these sulfonated pinene derivatives. U.S. Pat. Nos. 4,224,240 and 4,283,347, however, mention the possible utility of p-menth-1-ene-7-sulfonate salts as detergents and surfactants.

It is an object of the present invention to provide non-petroleum derived sulfonate salts useful as hydrotropes in aqueous formulations.

It is a further object of this invention to disclose novel menthane sulfonate salts.

SUMMARY OF THE INVENTION p-Menthane-7-sulfonic acid and p-menthane-2-sulfonic acid and their alkali metal, alkaline earth metal, ammonium and alkylolammonium salts are hereby disclosed.

Furthermore, a method for increasing the solubility of an only partially water-soluble material is provided comprising combining with said material in water a hydrotrope selected from the group consisting of the alkali metal, alkaline earth metal, ammonium and alkylolammonium salts of p-menth-6-ene-2-sulfonic acid, p-menth-1-ene-7-sulfonic acid and their saturated derivatives.

DETAILED DESCRIPTION OF THE INVENTION

Salts of four $\alpha$- and $\beta$-pinene derived sulfonates have been identified as effective hydrotropes in aqueous media. These compounds are identified by their structural formulas below:

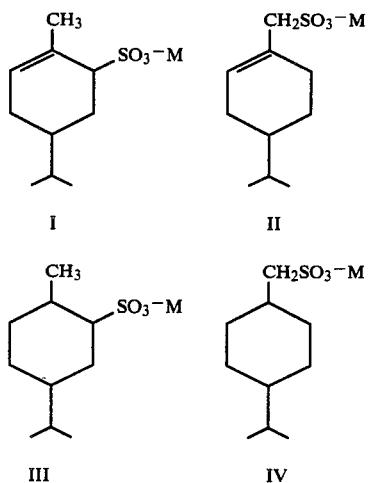

where M is an alkali metal, alkaline earth metal, ammonium or alkylolammonium cation.

According to Traynor et al in the J. Org. Chem. article, compound I could not, by sulfonation, be prepared directly from $\alpha$-pinene. Competitive acid isomerization and hydration to $\alpha$-terpineol was said to occur. These investigators were forced to prepare compound I by the circuitous route of epoxidizing $\alpha$-pinene. The epoxide was then reacted with sulfite, acidified by ion-exchange chromatography and dehydrated to obtain I.

Now it has been found that compound I can be directly prepared from $\alpha$-pinene at atmospheric pressure. The procedure involves incremental additions of bisulfite or sulfite to aqueous or mixed aqueous-organic co-solvent, pinene solutions in the presence of air or a free radical initiator.

Where the ammonium salts of sulfite or bisulfite are employed, oxygen is the preferable free radical initiator. These reactions readily occur at atmospheric pressure.

Sodium sulfite or bisulfite reactions are preferably initiated by organic or inorganic peroxides. Representative of the former type free radical initiators are tert-butyl peroxide, benzoyl peroxide, cumene hydroperoxide, tetralin hydroperoxide, isopropylbenzene hydroperoxide, acetyl peroxide, urea peroxide, methylethyl ketone peroxide, diisopropyl ether peroxide, diisopropyl peroxy dicarbonate, and, preferably tert-butyl peroxy benzoate. Inorganic initiators such as hydrogen peroxide, hydrazine sulphate, sodium percarbonate and sodium persulphate are also useful. Organic diazo initiators, such as azobisisobutyronitrile, may similarly be employed. The free radical initiators are preferably combined with the sulfite or bisulfite and incrementally added to the $\alpha$- or $\beta$-pinene. Generally, from about 0.1 to about 10 mole %, based on moles pinene, of the free radical initiator are used in the reaction mixture. Additionally, ultraviolet radiation may serve to establish the free radical conditions, including when a ultraviolet photo-initiator is added to the reaction mixture.

Although water can be used as the exclusive solvent, mixed water-organic co-solvent systems are preferred. The organic co-solvents should be non-reactive in the process. Such solvents include alcohols, ethers, glycol ethers, esters, glycols, amines, amino alcohols and mixtures thereof. A combination of water with isopropanol is preferred. Mixed aqueous-organic co-solvent systems may be combined in ratios ranging from 100:1 to 1:100.

Preferably, the ratio of water to co-solvent should range from about 1:4 to 1:1. Water is present to assist the solubilization of the sulfite or bisulfite salt. Organic co-solvent is present for solubilizing the pinene. The amount of solvent, either water, organic co-solvent or mixtures thereof, relative to the pinene reactant will range from 100:1 to 1:100, respectively.

Reaction temperatures should range from at least 40° C. to about 300° C. Preferably, the range should be from about 80° C. to 150° C.

Relative molar ratios of sulfite or bisulfite to pinene can range broadly from about 2:1 to 0.8:1. Preferably, their relative amounts should range from about 0.95:1 to 1.4:1, sulfite or bisulfite to pinene, respectively.

Yields of these reactions can be markedly improved where small amounts of phase transfer catalysts are included. Phase transfer catalysts are organic soluble quaternary ammonium or phosphonium salts. The cations assist in the transport of reactive anions from aqueous to organic phase. The phosphonium or ammonium cations generally contain at least one hydrophobic moiety such as a $C_7$-$C_{24}$ alkyl, phenyl or benzyl group. Illustrative of these materials are tricaprylylmethylammonium chloride and hexadecyltributylphosphonium bromide. Particularly effective in the instant invention is benzyltrimethylammonium hydroxide. Their concentration can vary from 0.01 to 20 mole percent, based on pinene reactant. Preferably, they are present from 0.5 to 10 mole percent. Yields are increased by a factor of 10 in the sodium bisulfite reactions with α-pinene. Smaller, but still significant, yield increases are noted where the reactant is β-pinene.

Ammonium sulfite provides better yields than alkali metal sulfites or bisulfites. Ammonium bisulfite further improves yields and permits reaction to occur at lower temperatures, i.e., 40°-50° C. Aqueous 45% ammonium bisulfite solutions may be utilized at the commercially available pH of 5.0–5.2 or adjusted to pH 5.6–6.0 with ammonia. Upon completion of the reaction, solvent is removed. In the α-pinene reaction, a crystalline monohydrate of the trans isomer of compound I is isolated. Some cis isomer is separated as a resinous dark yellow material. With ammonium bisulfite solutions of pH above 5.5, the trans isomer is formed in high specific purity. Trace amounts of cis isomer form at pH 5.0–5.3. The cis-sulfonate behaves differently from the trans, the former being susceptible to auto-oxidation.

Compounds I and II can be converted to their saturated analogs III and IV through hydrogenation. A variety of hydrogenation methods and catalysts can be employed. Both soluble and heterogeneous catalysts are suitable. Among the heterogeneous variety are included platinum, palladium, rhodium, ruthenium, iridium and nickel, each metal being supported on suitable substrates to facilitate in the uptake of gaseous hydrogen. Particularly preferred is 5% palladium on charcoal. With this catalyst, hydrogen is preferably held at about 100 psi. Temperature is maintained around 80° C. over a 1–5 hour period.

In certain instances, to save expensive catalyst, it becomes advisable to remove sulphur poisons by pre-treatment with Raney Nickel. Pre-treatment involves stirring I or II with Raney Nickel in water at 45°–50° C.

Ammonium and alkylammonium salts of III and IV may be obtained by treatment of the corresponding hydrogenated sodium salt by passage through an ion exchange column and neutralization of the liberated sulfonic acid with the appropriate base (e.g., ammonium hydroxide or alkylolamines such as ethanolamine, diethanolamine and triethanolamine).

Sulfonates III and IV have better storage stability than their unsaturated precursors. Upon prolonged storage, compounds I and II developed a yellow color.

Compounds I through IV are here shown to be effective hydrotropes for solubilizing only partially water-soluble materials into aqueous systems. Hydrotropes are commercially important, in particular, as components in aqueous cleaning compositions. These compositions frequently contain surfactants such as anionic, nonionic, cationic, zwitterionic or amphoteric actives or mixtures thereof. These surfactants are set forth in "Surface Active Agents and Detergents" by Schwartz, Perry & Berch, Vol. II, Interscience Publishers, Inc., 1958, herein incorporated by reference. These surfactants are generally employed at from 1% to 50% by weight of the total cleaning formulation.

Stability Performance Evaluation

A measure of the effectiveness of a hydrotrope is the amount required to stabilize a liquid composition undergoing freeze-thaw cycling.

The procedure for evaluating freeze-thaw stability involves subjecting a sample in a glass jar to six controlled freeze-thaw cycles between 0° F. and 70° F. Typically, inspection of samples is performed after each 1, 2, 3 and 6 cycles. Cycling time between 0° F. and 70° F. is 24 hours, except over weekends when temperature is maintained at 70° F. for 48 hours. Six hours are necessary for the temperature in the room to drop from 70° F. to 0° F. and 4 hours to rise from 0° F. to 70° F. These cycles are thought to simulate the most extreme conditions for storage and transportation of hydrotrope containing commercial products during winter months.

The following examples will more fully illustrate the embodiments of this invention. All parts, percentages and proportions referred to herein and in the appended claims are by weight unless otherwise indicated.

EXAMPLE 1

A typical light duty liquid dishwashing formulation is outlined in Table I. Into this base formulation were incorporated the various hydrotropes of this invention.

TABLE I

| Base Formulation | |
|---|---|
| Components | Weight % |
| Ammonium linear $C_{10}$-$C_{15}$ alkylbenzene sulfonate | 24.1 |
| Ammonium linear $C_{10}$-$C_{15}$ alcohol triethoxysulfate | 4.7 |
| Lauric diethanolamide | 3.0 |
| Hydrotrope* | — |
| Water | to 100 |

*Identity and amounts as per following Examples.

EXAMPLE 2

Compounds I, II, III and IV were evaluated for their efficiency as hydrotropes in freeze-thaw stability tests. These compounds were incorporated into the base formulation of Table I at several concentrations to determine the minimum amount hydrotrope needed to provide adequate stability. Ammonium xylene sulfonate served as the reference hydrotrope.

TABLE II

Freeze-Thaw Stability Performance

| Formulation | Hydrotrope | Concentration Weight % | Freeze-Thaw Stability (6 cycles at 0-70° F.) |
| --- | --- | --- | --- |
| 1 Control | Ammonium xylene sulfonate | 8 | Stable |
| 2 | Sodium salt of I | 8 | Stable |
| 3 | Ammonium salt of I | 8 | Stable |
| 4 | Sodium salt of III | 8 | 10-15% gel |
| 5 | Ammonium salt of III | 8 | 20% gel |
| 6 | Ammonium salt of III | 12 | 12% gel |
| 7 | Sodium salt of II | 8 | 10% gel on top |
| 9 | Ammonium salt of II | 8 | 8% gel on top |
| 10 | Ammonium salt of II | 9 | 10% gel on top |
| 11 | Ammonium salt of II | 10 | thin film of gel |
| 12 | Ammonium salt of II | 12 | Stable |
| 13 | Sodium salt of IV | 8 | 10-15% gel |
| 14 | Ammonium salt of IV | 8 | 15% gel |
| 15 | Ammonium salt of IV | 10 | 3-5% gel |
| 16 | Ammonium salt of IV | 12 | Stable |

Table II indicates that compounds I-IV all display hydrotrope properties. They approach ammonium xylene sulfonate in performance. At the 12% level, compound II and its saturated analog IV provided stable liquids under freeze-thaw conditions. Compound I provided equivalent stability to that of the control at 8% active concentration. The saturated analog, III, was less effective.

EXAMPLE 3

Preparation of (−) Sodium(2S,4R)p-menth-6-ene-2-sulfonate (I)

Method (1)

In a 2 liter, 3-neck Morton flask equipped with stirrer and reflux condenser, 136 g (1 mole) α-pinene and one liter isopropanol:water in the ratio 1:1 were brought to reflux. Sodium bisulfite, 110 grams (1.06 mole) was added at the rate of 26 grams per hour along with several additions of 2-3 drops t-butyl peroxybenzoate. The solution was refluxed for 10 hours.

Thereafter, the solution was evaporated to dryness and the residue extracted with hot 3A ethanol. Extraction was done three times with 500 ml solvent each time. The combined extracts were evaporated and the residual solids were then dried in vacuo over phosphorus pentoxide. A yield of 6% was obtained. The NMR spectrum exhibited the following peaks: $CH_3$ (doublet, 0.75 and 0.86$\delta$); $CH_3$ (singlet, 1.84$\delta$); $CH_2$ and CH (multiplet, 1.00-2.40$\delta$); CH (multiplet, 3.23-3.50$\delta$); and CH (multiplet, 5.50-5.62$\delta$).

Method (2)

In a 1-liter, 3-neck Morton flask, 130 g of α-pinene and 10 g of t-benzyltrimethyl ammonium hydroxide were dissolved in 400 ml of 1:1 isopropanol:water and brought to reflux. Sodium bisulfite, 120 g (1.15 mole) was added at the rate of 10 grams per hour along with several additions of 2-3 drops t-butyl peroxybenzoate. The solution was heated for 14 hours. The solvents were then removed by distillation. The residue was extracted with 3A ethanol. Extracts were combined and evaporated to dryness. Residues were dried in vacuo over phosphorus pentoxide. Crude product in the amount of 130 grams was obtained. Karl Fisher analysis indicated the presence of 2.9% water. NMR indicated 58% purity.

EXAMPLE 4

Preparation of (−) Ammonium(2S,4R)p-menth-6-ene-2-sulfonate (I)

Ammonium Sulfite Method

In a 3 liter flask equipped with stirrer, 136 g (1.0 mole) α-pinene was dissolved in 800 g isopropanol and 200 g water. The solution was brought to reflux. Ammonium sulfite monohydrate, 132 g (0.97 mole), was added at the rate of about 0.5 grams per minute. This solution was then refluxed for 15 hours. Thereafter, the solution was filtered, evaporated to dryness in vacuo and dried over phosphorous pentoxide. A product weighing 179 grams was obtained. NMR analysis indicated 81% purity (62% yield). Karl Fisher analysis showed 1.6% water present.

EXAMPLE 5

Preparation of (−) Ammonium(2S,4R)p-menth-6-ene-2-sulfonate (I)

Ammonium Bisulfite Method

Into a 500 ml flask equipped with a magnetic stirrer was placed 55 g α-pinene, 100 ml isopropanol, 150 ml water and 2 g (60%) benzyltrimethyl ammonium chloride. While stirring, 120 g (45%) ammonium bisulfite was gradually added. The mixture was stirred for 24 hours at 40°-45° C. Solvents were then removed by distillation in vacuo. The residue was dissolved in 300 ml isopropanol. The isopropanol solution was filtered and evaporated to dryness. A product weighing 93 grams was isolated. Its purity was 82.5% corresponding to an 81% yield.

EXAMPLE 6

Preparation of (−) Sodium(4S)-p-menth-1-ene-7-sulfonate (II)

Experiment (1)

A mixture of 140 g (1.03 moles) β-pinene and 650 ml water was heated to reflux in a 2 liter, 3-necked flask equipped with stirrer and reflux condenser. Then, 125 g (1.2 moles) sodium bisulfite was added in 25 gram increments per hour along with several additions of 2-3 drops t-butyl peroxybenzoate. Heat was applied to the mixture for a period of 7½ hours. The solution was allowed to stand overnight. Crystals which had formed were filtered off and dried in vacuo over phosphorus pentoxide. A total of 89 grams were collected having 91% purity (NMR analysis) indicating a 32% yield. The NMR spectrum of the compound included signals at: $CH_3$ (doublet, 0.75 and 0.85$\delta$); CH and $CH_2$ (multiplets, 1.00-2.40$\delta$); $CH_2$ (singlet, 3.40$\delta$); and CH (broad singlet, 5.80-5.90$\delta$).

Experiment (2)

In a 1 liter, 3-neck flask, 70 grams (0.51 mole) β-pinene and 325 ml water was heated to reflux. Sodium bisulfite, 70 grams, was added at the rate of 13 grams per hour. The solution was refluxed for 7 hours and allowed to stand overnight.

Excess β-pinene, 3.8 grams, was removed by distillation along with 100 ml of water. Upon cooling the solution, 106 grams (95% pure) of product was crystallized. The solution was evaporated to dryness and residue extracted with 300 ml hot ethanol. Ethanol was removed by distillation and residual solvent evaporated in vacuo. The product remained as a residue of 6.7 grams weight and 21.2% purity. Total yield was 87%.

EXAMPLE 7

Preparation of (−) Ammonium(4S)-p-menth-1-ene-7-sulfonate (II)

Ammonium Sulfite Method

A solution of 136 g (1 mole) β-pinene in 600 g isopropanol and 200 g water was heated to reflux in a 2 liter, 3-neck Morton flask. Ammonium sulfite monohydrate, 132 g (0.99 mole) was added at the rate of about 0.5 grams per minute. The solution was refluxed for a total of 15 hours. Thereafter, the solution was filtered, the filtrate being evaporated to dryness. There was obtained 156 grams product having 72.1% purity (47% yield).

The solid product was redissolved in 3A ethanol. Solvent insoluble residues were filtered off. Filtrate solvent was evaporated to dryness. Residue product was dried in vacuo over phosphorus pentoxide. A product was obtained having 74.7% purity by NMR analysis. Karl Fisher titration indicated 1.5% water.

EXAMPLE 8

Preparation of (−) Ammonium(4S)-p-menth-1-ene-7-sulfonate (II)

Ammonium Bisulfite Method

Into a 1 liter flask equipped with magnetic stirrer were placed 450 ml isopropanol, 240 ml water and 54.4 grams (0.4 mole) β-pinene. Ammonium bisulfite, 105 grams (45%) was then added thereto. The mixture was stirred at 40°–45° C. for 22 hours. Thereafter, the solution was evaporated to dryness. Residue was extracted with methanol. The methanolic solution was filtered, and the resultant filtrate evaporated to dryness. Obtained were 84 grams product (85.8% purity; 77% yield).

EXAMPLE 9

Preparation of Sodium p-menthane-2-sulfonate (III)

Sodium p-menth-6-ene-2-sulfonate (51.2 g) as prepared in Method 2 was dissolved in 500 ml water and mixed with 22.08 grams of Raney Nickel catalyst at 45°–50° C. Sulphur poisons were removed by this pretreatment.

After 2 hours, the mixture was filtered and transferred to a 1 liter Parr bomb. Twelve grams of 5% palladium on carbon were added to the mixture. The bomb was sealed and flushed several times with hydrogen. Hydrogenation was performed at 75°–80° C. for 3–4 hours at 100 psi. Thereafter, the bomb was cooled, opened and the solution filtered. Filtrate was evaporated to dryness and the residue stored over phosphorus pentoxide. The product weighing 42.4 grams, was 95.4% pure by NMR analysis. The NMR spectrum exhibited signals at: $CH_3$ (doublet, 1.04 and 1.12$\delta$); $CH_2$ and CH (multiplet, 1.20–2.50$\delta$); $CH_3$ (multiplet, 1.60$\delta$); and CH (multiplet, 3.00–3.20$\delta$).

EXAMPLE 10

Preparation of Ammonium p-menthane-2-sulfonate (III)

Sodium-p-menthane-2-sulfonate, 35 grams, prepared as in Example 9 was passed through an ion-exchange column. The eluate containing p-menthane-2-sulfonic acid was neutralized with dilute ammonium hydroxide. The solution was evaporated to dryness and the residue stored in vacuo over phosphorus pentoxide. The product was 91.7% pure by NMR analysis.

EXAMPLE 11

Preparation of Sodium (4S)-p-menthane-7-sulfonate (IV)

Sodium (4S)-p-menth-1-ene-7-sulfonate, 75 grams, was dissolved in 500 ml of water. The solution was then placed into a 1 liter Parr Reactor together with 12 grams (5%) palladium on carbon. The Parr Reactor was sealed and flushed with hydrogen gas several times to remove oxygen. Hydrogen was charged to the bomb at 100 psi and the contents heated to 75°–80° C. for 2 hours. Subsequently, the bomb was cooled, opened and the solution filtered to remove catalyst. Solvent was evaporated from the solution and the residue dried in vacuo over phosphorus pentoxide. Seventy grams of product with NMR purity of 99.3% was obtained. The NMR spectrum exhibited signals at: $CH_3$ (doublet, 1.00 and 1.14$\delta$); CH and $CH_2$ (multiplet, 1.00–1.30$\delta$); and $CH_2$ (triplet, centered at 3.07$\delta$).

EXAMPLE 12

Preparation of Ammonium (4S)-p-menthane-7-sulfonate (IV)

An aqueous solution of 30 grams sodium (4S)-p-menthane-7-sulfonate, prepared according to Example 11, was passed through a Permutit Q101 cationic exchange column to remove sodium ions. The eluate containing (4S)-p-menthane-7-sulfonic acid was neutralized with ammonium hydroxide solution. The resultant residue was dried over phosphorus pentoxide. Obtained were 29 grams product of 99.9% purity.

The foregoing description and examples illustrate selected embodiments of the present invention and in light thereof variations and modifications will be suggested to one skilled in the art, all of which are in the spirit and purview of this invention.

What is claimed is:

1. A method of increasing the solubility of an only partially water-soluble material, said material being present in an amount from 1% to 50% and selected from the group consisting of anionic, nonionic, cationic, zwitterionic, amphoteric surfactants and mixtures thereof, comprising combining with said material in water, in an effective amount to increase said solubility, a hydrotrope selected from the group consisting of the alkali metal, alkaline earth metal, ammonium and alkylolammonium salts of p-menth-6-ene-2-sulfonic acid, p-menth-1-ene-7-sulfonic acid and their saturated derivatives.

2. A method according to claim 1 wherein the partially water-soluble material is a component of a cleaning formulation.

3. A method according to claim 1 wherein the concentration of said hydrotrope ranges from 8% to 12%.

* * * * *